(12) United States Patent
Lutz

(10) Patent No.: US 8,759,083 B2
(45) Date of Patent: Jun. 24, 2014

(54) BIOREACTOR FOR METHANIZATION OF BIOMASS HAVING A HIGH SOLIDS FRACTION

(75) Inventor: Peter Lutz, Münich (DE)

(73) Assignee: Bekon Energy Technologies GmbH & Co., KG, Unterfohring (DE)

( * ) Notice: Subject to any disclaimer, the term of this patent is extended or adjusted under 35 U.S.C. 154(b) by 394 days.

(21) Appl. No.: 12/280,159

(22) PCT Filed: Feb. 21, 2007

(86) PCT No.: PCT/EP2007/051686
§ 371 (c)(1),
(2), (4) Date: Oct. 22, 2008

(87) PCT Pub. No.: WO2007/096392
PCT Pub. Date: Aug. 30, 2007

(65) Prior Publication Data
US 2009/0068725 A1    Mar. 12, 2009

(30) Foreign Application Priority Data
Feb. 21, 2006  (DE) .............. 20 2006 002 757 U

(51) Int. Cl.
*C12M 1/107* (2006.01)
*C12M 1/34* (2006.01)
*C12M 1/00* (2006.01)
*C12M 1/16* (2006.01)
*C12M 1/12* (2006.01)

(52) U.S. Cl.
CPC .............. *C12M 21/04* (2013.01); *C12M 21/16* (2013.01); *C12M 23/58* (2013.01); *C12M 29/02* (2013.01); *C12M 41/44* (2013.01); *C12M 25/18* (2013.01); *Y02E 50/343* (2013.01)
USPC ................ 435/290.4; 435/287.5; 435/289.1; 435/300.1; 210/601; 210/767

(58) Field of Classification Search
CPC ...... C12M 21/04; C12M 21/16; C12M 23/58; C12M 25/18; C12M 29/02; C12M 41/44
USPC ..................... 435/290.4, 287.5, 289.1, 300.1; 210/601, 767
See application file for complete search history.

(56) References Cited

U.S. PATENT DOCUMENTS

| | | | |
|---|---|---|---|
| 4,396,402 A | 8/1983 | Ghosh | |
| 4,565,552 A | 1/1986 | Cotton | |
| 5,403,742 A | 4/1995 | Freeman | |
| 5,773,526 A | 6/1998 | Van Dijk et al. | |
| 6,110,727 A * | 8/2000 | Widmer et al. | 435/262 |
| 6,254,775 B1 * | 7/2001 | McElvaney | 210/603 |
| 6,569,332 B2 * | 5/2003 | Ainsworth et al. | 210/603 |
| 6,699,708 B1 | 3/2004 | Muller et al. | |
| 7,604,988 B2 | 10/2009 | Daly | |
| 7,854,840 B2 | 12/2010 | Busch et al. | |
| 8,053,228 B2 | 11/2011 | Lutz | |

FOREIGN PATENT DOCUMENTS

| | | |
|---|---|---|
| DE | 224 023 A1 | 6/1985 |
| DE | 3719564 A1 | 12/1988 |
| DE | 4444462 A1 | 6/1996 |
| DE | 195 32 359 A1 | 3/1997 |
| DE | 196 43 142 C1 | 12/1997 |
| DE | 19833624 A1 | 1/2000 |
| DE | 202 03 533 U | 11/2002 |
| DE | 10129718 | 2/2003 |
| DE | 20121701 U1 | 3/2003 |
| DE | 102 37 663 A1 | 8/2003 |
| DE | 103 02 658 A1 | 7/2004 |
| DE | 10257849 | 7/2004 |
| DE | 203 19 847 U | 9/2005 |
| DE | 10 2004 053615 B3 | 5/2006 |
| DE | 202005014176 U | 10/2006 |
| EP | 0 023 176 A2 | 1/1981 |
| EP | 0 142 473 A2 | 5/1985 |
| EP | 0 142 473 A3 | 5/1985 |
| EP | 0 142 473 B1 | 5/1985 |
| EP | 0803568 | 10/1997 |
| EP | 1301583 B1 | 8/1999 |
| FR | 2502174 A1 | 9/1982 |
| JP | 2004-511331 A | 4/2004 |
| JP | 2004-513621 A | 5/2004 |

| | | | |
|---|---|---|---|
| JP | 2005-296905 A | 10/2005 | |
| WO | WO 02/06439 | * | 1/2002 |

OTHER PUBLICATIONS

Wang et al., "Influence of Hydraulic Retention Time on Anaerobic Digestion of Pretreated Sludge", Biotechnol. Tech. 11(2), pp. 105-108, 1997.*
Translation of WO 02/06439, Jan. 2002.*
Chinese Office Action mailed Dec. 24, 2010, for CN Application No. 200680032916.9, with English Translation, 11 pages.
European Search Report mailed Mar. 2, 2011, for EP Application No. 10185759.7, four pages.
Notification of Reason(s) for Refusal mailed Jul. 6, 2010, for JP Application No. 2008-529558, English Translation, four pages.
Chinese Office Action mailed Mar. 23, 2011, for CN Application No. 200780006221.8, with English Translation, 8 pages.
Notification of Reason(s) for Refusal mailed Mar. 29, 2011, for JP Application No. 2008-554791, with English Translation, four pages.
Anonymous. (Feb. 2004). "Dry Fermentation—Evaluation of Research and Development Needs," *Proceedings of Gülzower Trade Talks*, Feb. 4-5, 2004, Gülzow, vol. 23, Fachagentur Nachwachsende Rohstoffe (FNR), 21 pages (English Translation of Description Only.).
Anonymous. (Feb. 2006). "Dry Fermentation—State of Development and Further R&D Needs," *Proceedings of Gülzower Trade Talks*, Feb. 4-5, 2006, Gülzow, vol. 24, Fachagentur Nachwachsende Rohstoffe (FNR), 143 pages. (English Translation of Description Only.).

* cited by examiner

*Primary Examiner* — Nathan Bowers
*Assistant Examiner* — Gautam Prakash
(74) *Attorney, Agent, or Firm* — Morrison & Foerster LLP

(57) ABSTRACT

A bioreactor having improved gas yield is described, wherein the necessary residence time of the biomass in the digestion tank is reduced. During the fermentation of dry, i.e. non-pumpable biomass, percolating juices, so-called percolate, is generated as a result of the moisture contained in the biomass, which percolate is withdrawn via a drainage system and, if necessary, recirculated from the top onto the biomass to be fermented. It has now been found that the biomass yield is significantly increased—in the region of between 10% and 40%—when the resultant percolate is not immediately withdrawn by way of the drainage system, but is accumulated in the digestion tank up to a specific level. This is achieved by a technical device wherein the digestion tank is liquid-tight, i.e. also the flap for loading and unloading the digestion tank must be liquid-tight and also be designed in a correspondingly solid manner in order to withstand the resultant liquid pressure. By linking the existing percolate drainage system with a percolate control system it is possible to adjust and control the liquid level of the percolate in the fermenting biomass in such a way that the biogas generation rate or the biogas yield is maximized.

18 Claims, 4 Drawing Sheets

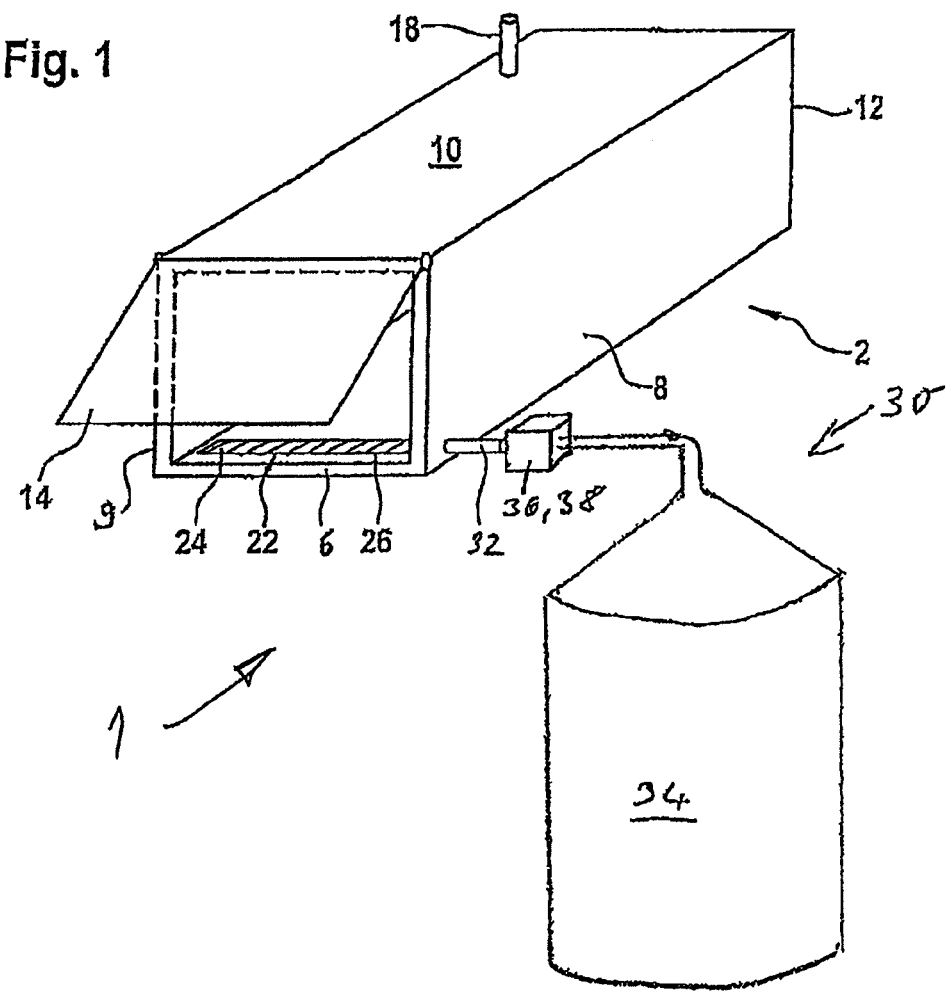

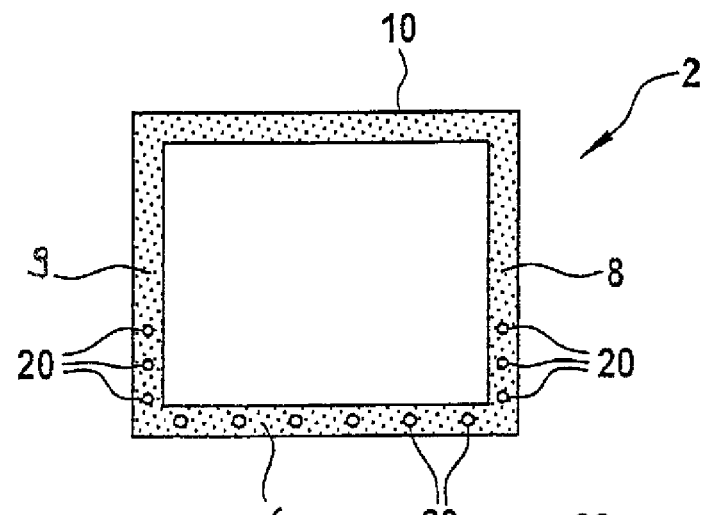
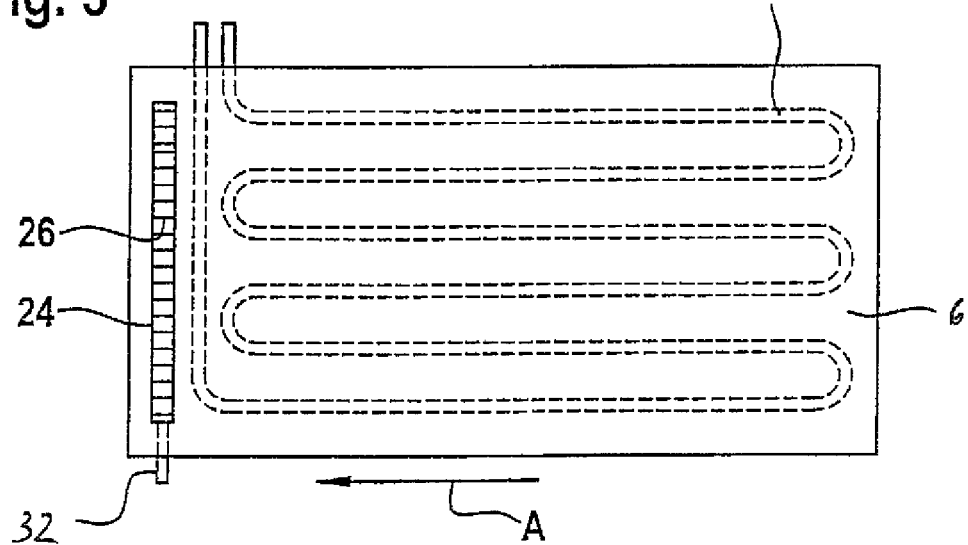

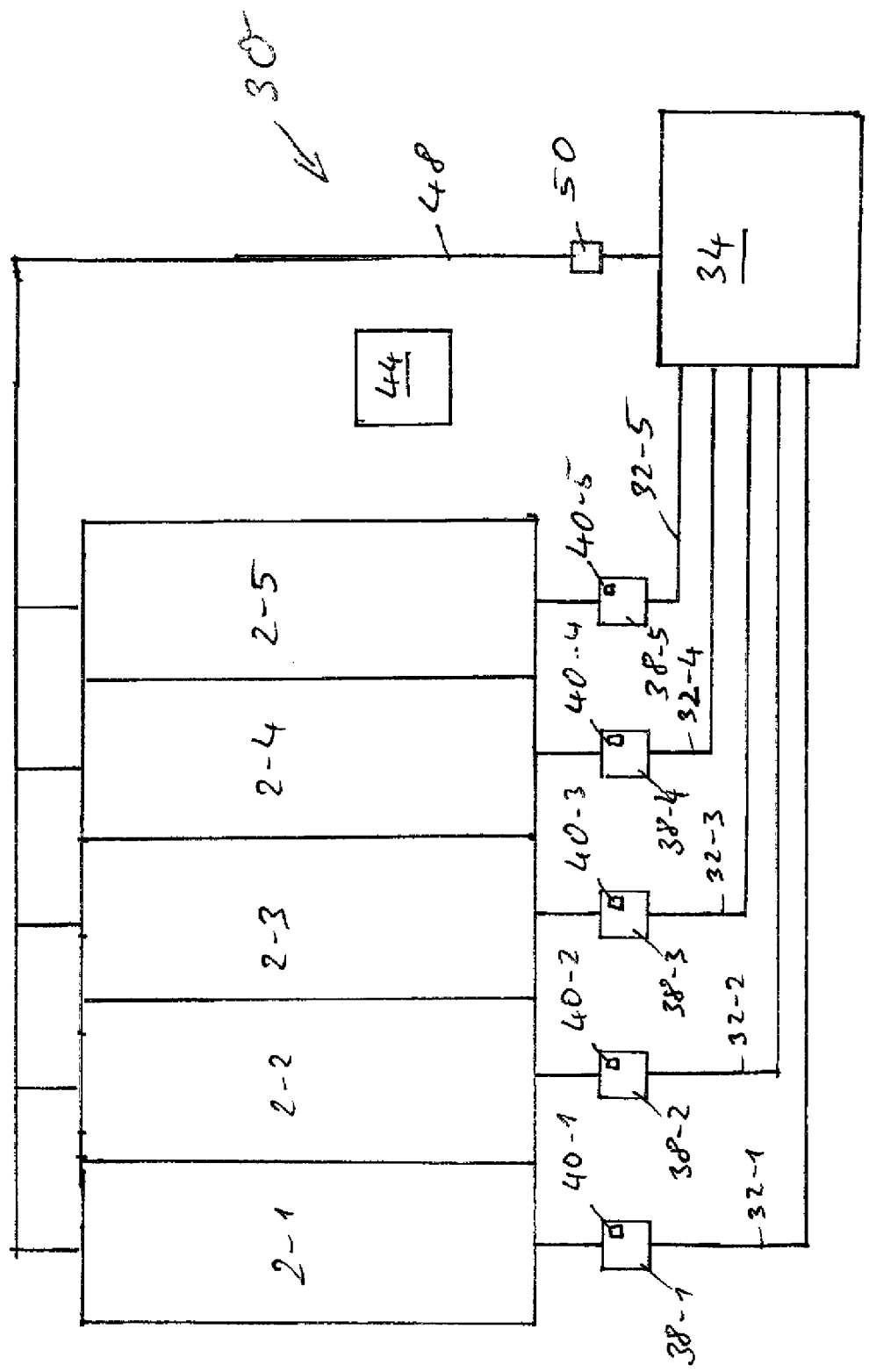

BIOREACTOR FOR METHANIZATION OF BIOMASS HAVING A HIGH SOLIDS FRACTION

CROSS-REFERENCE TO RELATED APPLICATIONS

This application is a United States National Stage Application under 35 U.S.C. §371 of International Patent Application No. PCT/EP2007/051686, filed Feb. 21, 2007, which claims the benefit to German Patent Application No. 20 2006 002 757.2, filed Feb. 21, 2006, each of which is incorporated by reference into this application as if fully set forth herein.

FIELD OF INVENTION

The invention relates to a bioreactor for methanizing biomass having a high solids fraction.

BACKGROUND OF INVENTION

The term "biomass having a high solids fraction" is to be understood as meaning the opposite of liquid, pumpable biomass, such as is used in wet fermentation processes. "Biomass having a high solids fraction" is therefore to be understood as non-pumpable biomass.

A bioreactor is known from patent document EP 1 301 583 B1, the entire disclosed content of which is referred to herein in order to avoid unnecessary repetition and the disclosed content of which is expressly incorporated into the present application.

This well-known bioreactor comprises a digestion tank in the like of a prefabricated garage, which is sealed in a gas-tight manner by means of a flap. The loading with unfermented biomass and the unloading of the fermented residual biomass can take place by means of a wheel loader. Because the biomass settles during the fermentation process, the biomass presses against the flap. The flap must therefore be built in a correspondingly solid manner and must otherwise also close in a precise manner in order to sufficiently seal off the digestion tank. Such a flap that is solidly built and, at the same time, capable of moving with precision is expensive. In addition, there is a risk of the flap no longer sealing and closing with precision in the case of high loading with biomass. In order to solve this problem, patent document DE 202005014176.3 proposes a retaining system behind the flap, which prevents the settling biomass from pressing against the flap.

In patent document DE 102 57 849 A1, there is described a garage fermenter, wherein the biomass is aerated with biogas from the bottom through a screen base. This screen base accordingly also acts as draining system for the percolate, which, as in our case, is also circulated by means of a pump. A control of the fill level is, however, not mentioned.

Patent document DE 101 29 718 A1 describes a vertical fermenter for methanizing domestic biowaste using continuous charging and withdrawal through separate openings by means of a screw conveyor. The percolate is separated off using a screen base and circulated by means of a pump, but with the fill level of the percolate not being controlled.

Patent document DE 44 44 462 A1 also relates to a vertical fermenter, wherein the biomass is filled in at the top in a discontinuous and gas-tight manner, sinks down during the fermentation and is withdrawn at that location in a discontinuous and gas-tight manner. A controlled seepage water recirculation is used in order to transport the organic acids formed at the top to the lower region of the reactor, where the fermentation takes place. The solid fraction of the biogenic material is stated to be 30% to 55%.

In patent document DE 201 21 701 U1, there is described a two-step system comprising two reactors. In the first reactor, in a wet process the biomass is held swimming in a processing liquid containing anaerobic bacteria and thereby transported from one feed opening to a withdrawal opening. The processing liquid is sprinkled onto the biomass by way of recirculation. The processing liquid is transferred into a second reactor and fermented therein. However, biogas is generated in both reactors. As an alternative to the wet process, it is also possible to process biomass having a high solids fraction in the first reactor. In this case, biogas is mainly generated in the second reactor. A control of the fill level for the processing liquid is not mentioned.

Patent document EP 0 803 568 A1 describes a biogas plant for fermenting biomass having a solids fraction of approximately 25% dry matter. The plant comprises a plurality of reactors which are connected among each other in such a way that material withdrawn from the reactors can be supplied in a targeted manner to other reactors in order to attain an individual and optimal process control in each reactor.

Patent document DE 37 19 564 A1 discloses a bioreactor according to the preamble of claim 1.

Although the gas yield from the biomass and the necessary residence time of the biomass is sufficient in many cases, a higher gas yield and/or a reduced residence time of the biomass in the digestion tank would be desirable.

BRIEF DESCRIPTION OF THE DRAWINGS

It is thus the object of the present invention to improve the bioreactor known from patent document EP 1 301 583 B1 in such a way that the gas yield is increased and the necessary residence time of the biomass in the digestion tank is reduced.

This object is solved by a bioreactor by virtue of characterising features.

Figure 4:
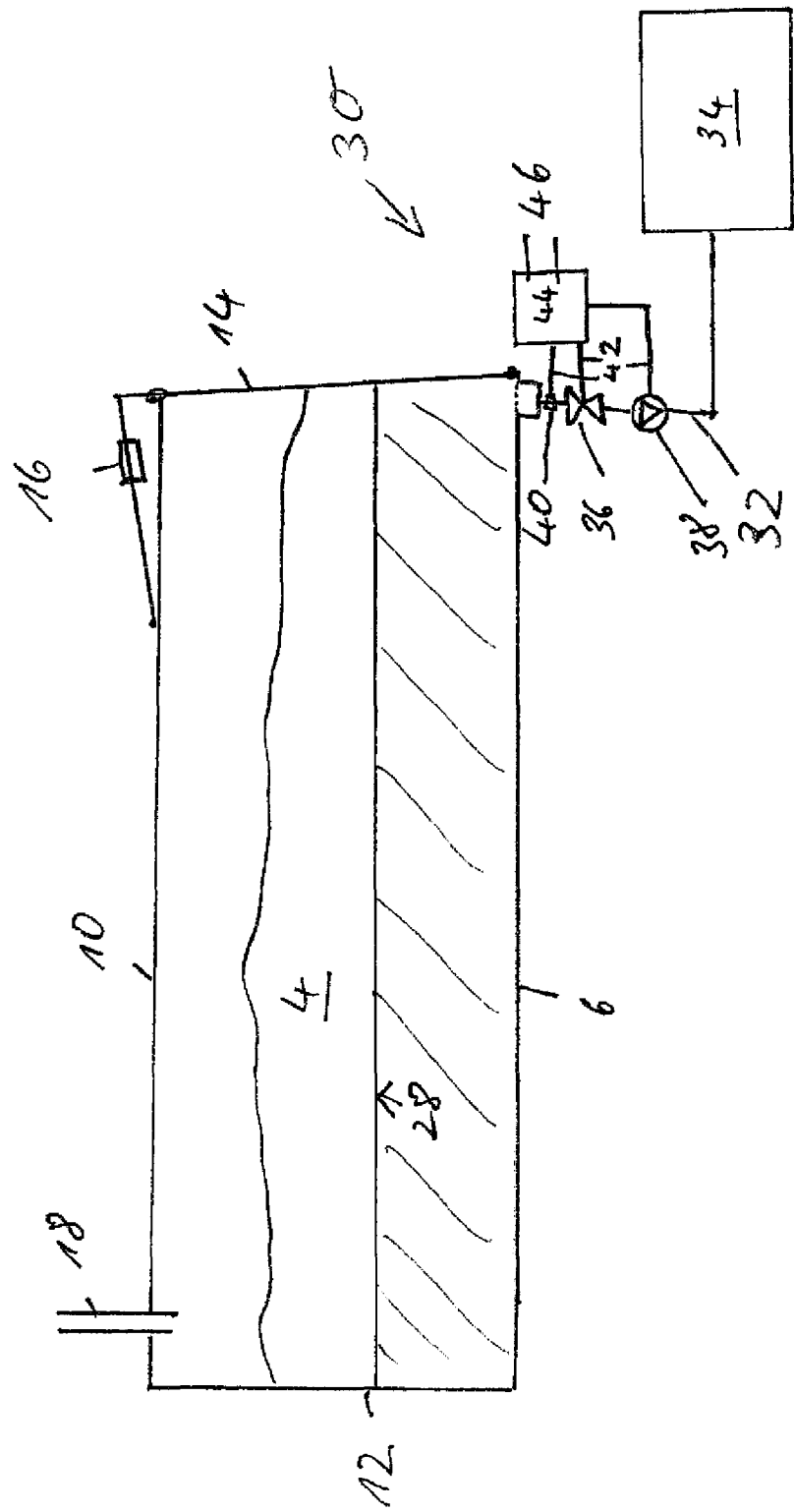

During the fermentation of dry, i.e. non-pumpable biomass, percolating juices, so-called percolate, are generated as a result of the moisture contained in the biomass, said percolate being withdrawn by way of a drainage system and, if necessary, returned again from the top onto the biomass to be fermented. It has now been found that the biomass yield is significantly increased—in the region of between 10% and 40%—when the resultant percolate is not immediately withdrawn by way of the drainage system, but is rather accumulated in the digestion tank up to a specific level. This is achieved by a technical device wherein the digestion tank is liquid-tight, i.e. also the flap for loading and unloading the digestion tank must be liquid-tight and also be designed in a correspondingly solid manner in order to withstand the resultant liquid pressure. By linking the existing percolate drainage system with a percolate control system it is possible to adjust and control the liquid level of the percolate in the fermenting biomass in such a way that the biogas generation rate or the biogas yield is maximized.

According to a preferred embodiment of the invention, the percolate control system comprises a percolate storage which is connected to the percolate drainage system via a percolate discharge conduit. A valve is disposed in the percolate discharge conduit, by means of which the percolate forming in the digestion tank can be accumulated to the desired height. In doing so, the height of the percolate level is adjusted in such a way that the gas yield is maximal. The discharge of the percolate into the percolate storage is driven by gravity.

According to an advantageous embodiment of the invention, a percolate pump is disposed in the percolate discharge conduit in order to enable the gravity-independent discharge of the percolate into the percolate storage. In this case, the percolate pump can, at the same time, also take over the function of the valve.

According to an advantageous embodiment of the invention, the fill level sensor is a simple pressure sensor, which is disposed in the percolate discharge conduit in the region of the base of the digestion tank. Such pressure sensors are very inexpensive and resistant against the chemically aggressive percolate.

According to a further preferred embodiment of the invention, the percolate control system also comprises a percolate return line in order to return percolate from the percolate storage back into the digestion tank in a manner known per se.

According to a further preferred embodiment of the invention, filling bodies are set in the percolate storage, in which biogas generating microorganisms can accumulate particularly well. This may be achieved in a simple manner by introducing a fixed bed of biomass having a high solids fraction into the percolate storage. In this way, also the percolate storage itself serves as bioreactor and biogas can be withdrawn from the percolate storage.

According to a further preferred embodiment, a multiplicity of the bioreactors according to the invention can be interconnected in order to provide a biogas generation system. The multiplicity of bioreactors then comprises a common percolate storage.

According to a preferred embodiment of the invention, in this case the individual bioreactors are connected among each other additionally by percolate connection lines. In this way, it is for example possible to adjust the same liquid level in the individual bioreactors.

Further details, features and advantages of the invention arise from the following description of exemplary embodiments of the invention with reference to the drawings.

In the figures,

FIG. 1 shows schematically a perspective view of the bioreactor according to the invention;

FIG. 2 shows a cross sectional view of the bioreactor according to FIG. 1 perpendicular to the loading and unloading direction;

FIG. 3 shows a schematic view of the base plate of the bioreactor from FIGS. 1 and 2, respectively;

FIG. 4 shows a schematic cross sectional view of the bioreactor according to the FIGS. 1 to 3; and FIG. 5 shows a schematic view of an exemplary embodiment of a biogas generation system comprising a multiplicity of bioreactors according to the invention.

The FIGS. 1 to 4 show an exemplary embodiment of a bioreactor or biogas reactor 1, as the case may be, according to the present invention. The bioreactor comprises a cuboid shaped digestion tank 2, which is filled with biomass 4. The digestion tank 2 is made of concrete in the like of a prefabricated garage and comprises six flat wall elements, in particular a base plate 6, two side walls 8 and 9, a cover plate 10, a rear wall 12 and an open front side 13, which is sealable by means of a gas-tight flap 14.

DETAILED DESCRIPTION OF PREFERRED EMBODIMENTS

The flap 14 can be actuated by means of a hydraulic mechanism 16. In the event that the flap 14 is open, it is possible in a simple manner to fill the digestion tank 2 or remove the residual biomass therefrom, as the case may be. The biogas generated in the digestion tank 2 is removed by way of a biogas discharge conduit 18. In the base plate 6 of the digestion tank 2 and to some extent also in the side walls 8 and 9 a heating system 20—see FIG. 3—in the like of an underfloor heating system can be provided, by means of which the biomass 4 present in the digestion tank 2 can be correspondingly temperature conditioned. As to details, reference is hereto made to the corresponding descriptions in the patent document EP 1 301 583 B1.

Also integrated in the base plate 6 is a percolating juice drainage system 22, which is realized by a slight inclination of the base plate 6 in the direction of flap 14 (shown as arrow "A" in FIG. 3) and by a channel 24, arranged in the front region of the digestion tank behind the flap 14. The channel 24 runs perpendicular to the longitudinal direction or loading and unloading direction of the digestion tank 2 and is covered by a perforated or slotted plate 26. Only one channel 24 is shown in the exemplary embodiment. Alternatively, a plurality of such channels can be provided, which can also be arranged perpendicularly or in longitudinal direction.

The height of the percolate level 28 is regulated and/or controlled by means of a percolate control system 30. The percolate control system 30 comprises a percolating juice or percolate discharge conduit 32, by means of which the percolate collecting in the channel 24 is discharged into a percolate storage 34. The percolate discharge conduit 32 can be closed off by means of a valve 36, so that the percolate collecting in the digestion tank 2 can be accumulated up to a desired level 28. A percolate pump 38 is disposed in the percolate discharge conduit 32 in order to enable the gravity-independent transport of the percolate into the percolate storage 34.

The height of the percolate level 28 in the digestion tank 2 is determined via a fill level sensor in the form of a pressure sensor 40. The pressure sensor 40 is disposed in the percolate discharge conduit 32 prior to the valve 36. The pressure sensor 40, the valve 36 and the percolate pump 38 are connected to a control unit 44 via control lines. By way of additional control lines 46, further process parameters such as e.g. the gas production rate, the gas pressure in the interior of the digestion tank, etc. can be supplied to the control unit 44. In this way the percolate level 28 can be adjusted by means of the control unit 44 in such a way that the gas production rate is maintained at a maximum value.

In FIG. 1, which only shows a schematic view of an embodiment of the invention, the percolate storage 34 is disposed under the digestion tank. Because a percolate pump 38 is provided in the percolate discharge conduit 32, the percolate storage 34 can also be disposed at the same height as the digestion tank 2.

In FIG. 4, the valve 36 is disposed in the discharge direction prior to the percolate pump 38. Alternatively, the valve 36 can also be disposed after the percolate pump 38. In this case, also the pressure sensor 40 can be disposed in the pump sump of the percolate pump 38. In the corresponding embodiment of the percolate pump 38, this pump can also take over the function of the valve 36, i.e. during standstill the percolate pump 36 closes off the percolate discharge conduit 32, to enable the percolate to be accumulated in the digestion tank.

FIG. 5 shows schematically a biogas generation system comprising five bioreactors and digestion tanks 2-1 to 2-5, respectively, in accordance with the FIGS. 1 to 4. The five digestion tanks 2-1 to 2-5 are connected by way of five percolate discharge conduits 32-1 to 32-5 to a common percolate storage 34. In each percolate discharge conduit 32-i there is arranged a percolate pump 38-i that also takes over the function of the valve 36 in the embodiment according to the FIGS. 1 to 4. A pressure sensor 40-i for determining the percolate level in the respective digestion tank 2-i is disposed in the pump sump of each of the individual percolate pumps 38-*i*. Percolate from the common percolate storage 34 can be returned into the respective digestion tanks 2-*i* by way of a percolate return line 48 comprising a percolate recirculation pump 50. The percolate level 28 can be controlled and regulated via a control unit 44. The control unit 44 is connected to the pressure sensors 40-1 to 40-5 and actuates the percolate pumps 38-1 to 38-5 and the percolate recirculation pump 50. The associated control lines run according to FIG. 4, but are not shown in FIG. 5 for reasons of clarity.

In addition, the digestion tanks 2-*i* can also be linked to one another by percolate lines (not shown).

The invention claimed is:

1. A bioreactor for methanizing non-pumpable biomass having a high solids fraction, comprising:
    a gas-tight sealable and liquid-tight digestion tank,
    a biogas discharge conduit,
    a loading and unloading opening for filling and emptying the digestion tank with the non-pumpable biomass,
    a percolate drainage system in the base and/or the walls of the digestion tank, and
    a percolate control system connected to the percolate drainage system, the percolate control system comprises:
        a percolate storage, which is connected to the percolate drainage system by way of a percolate discharge conduit,
        a valve disposed in the percolate discharge conduit, and
        a percolate fill level sensor for determining the percolate liquid level in the digestion tank separately from the fill level of the non-pumpable biomass in the digestion tank,
    the percolate control system is configured to control a biogas generation rate by adjusting the percolate liquid level in the digestion tank.

2. The bioreactor as claimed in claim 1, characterized in that the percolate control system comprises a percolate pump disposed in the percolate discharge conduit.

3. The bioreactor as claimed in claim 1 or 2, characterized in that the fill level sensor is a pressure sensor, which is disposed in the percolate discharge conduit or in the digestion tank.

4. The bioreactor as claimed in claim 1, characterized in that the percolate control system comprises a percolate return line which connects the percolate storage to the upper region of the digestion tank.

5. The bioreactor as claimed in claim 1, characterized in that the loading and unloading opening is a hydraulically actuable flap which seals the digestion tank in a flush manner.

6. The bioreactor as claimed in claim 5, characterized by a retaining device which is disposed in such a way in the digestion tank in filling direction behind the flap that the filled non-pumpable biomass supports itself at least partially against the retaining device.

7. The bioreactor as claimed in claim 1, characterized in that filling bodies are set in the percolate storage, onto which biogas generating microorganisms can attach themselves and that the percolate storage comprises a biogas withdrawal line.

8. The bioreactor as claimed in claim 7, characterized in that the filling bodies in the percolate storage form a fixed bed of biomass having a high solids fraction.

9. A biogas generating system comprising a multiplicity of bioreactors as claimed in claim 1 and a common percolate storage.

10. The biogas generating system as claimed in claim 9, characterized in that the majority of the individual bioreactors are connected with one another through percolate connection lines.

11. A method for using the bioreactor of claim 1 for methanizing non-pumpable biomass having a high solids fraction, comprising:
    filling the gas-tight sealable and liquid-tight digestion tank with the non-pumpable biomass through the loading and unloading opening, wherein percolate accumulates in the digestion tank;
    using the percolate fill level sensor to determine the percolate liquid level in the digestion tank separately from the fill level of the non-pumpable biomass in the digestion tank;
    controlling the biogas generation rate by adjusting the percolate liquid level in the digestion tank by the percolate control system linked to the percolate drainage system in the base and/or walls of the digestion tank, the percolate drainage system connected to a percolate storage by way of the percolate discharge conduit;
    removing the biogas generated in the digestion tank by the biogas discharge conduit; and
    emptying the digestion tank of the non-pumpable biomass through the loading and unloading opening.

12. The method as claimed in claim 11, comprising:
    closing off the percolate discharge conduit, by the valve or a percolate pump, to enable percolate to be accumulated in the digestion tank.

13. The method as claimed in claim 11, wherein the fill level sensor is a pressure sensor, which is disposed in the percolate discharge conduit or in the digestion tank.

14. The method as claimed in claim 11, comprising:
    returning percolate from the percolate storage back into the digestion tank by a percolate return line.

15. The method as claimed in claim 11, comprising:
    sealing the digestion tank in a flush manner by a hydraulically actuable flap of the loading and unloading opening.

16. The method as claimed in claim 15, wherein a retaining device is disposed in such a way in the digestion tank in filling direction behind the flap that the filled non-pumpable biomass supports itself at least partially against the retaining device.

17. The method as claimed in claim 11, wherein filling bodies are set in the percolate storage, onto which biogas generating microorganisms can attach themselves, and wherein the percolate storage comprises a biogas withdrawal line.

18. The method as claimed in claim 17, wherein the filling bodies in the percolate storage form a fixed bed of biomass having a high solids fraction.

\* \* \* \* \*